(12) United States Patent
Ogawa

(10) Patent No.: US 10,962,548 B2
(45) Date of Patent: Mar. 30, 2021

(54) METHOD FOR DETERMINING AND SYSTEM FOR DETERMINING POLYPEPTIDE BONDING TO TARGET MOLECULE

(71) Applicant: MOLCURE, INC., Tokyo (JP)

(72) Inventor: Ryu Ogawa, Tokyo (JP)

(73) Assignee: MOLCURE, INC., Tokyo (JP)

( * ) Notice: Subject to any disclaimer, the term of this patent is extended or adjusted under 35 U.S.C. 154(b) by 654 days.

(21) Appl. No.: 15/038,457

(22) PCT Filed: Nov. 21, 2014

(86) PCT No.: PCT/JP2014/080853
§ 371 (c)(1),
(2) Date: May 21, 2016

(87) PCT Pub. No.: WO2015/076355
PCT Pub. Date: May 28, 2015

(65) Prior Publication Data
US 2016/0291032 A1 Oct. 6, 2016

(30) Foreign Application Priority Data
Nov. 22, 2013 (JP) .............................. JP2013-242304

(51) Int. Cl.
*G01N 33/68* (2006.01)
*C12N 15/10* (2006.01)
*C12Q 1/6874* (2018.01)

(52) U.S. Cl.
CPC ..... *G01N 33/6818* (2013.01); *C12N 15/1037* (2013.01); *C12Q 1/6874* (2013.01); *G01N 33/6842* (2013.01); *G01N 33/6845* (2013.01)

(58) Field of Classification Search
None
See application file for complete search history.

(56) References Cited

FOREIGN PATENT DOCUMENTS

WO 2013/080055 A2 6/2013

OTHER PUBLICATIONS

New England BioLabs, Inc., "Phage Display," website: (https://www.neb.com/applications/protein-analysis-and-tools/phage-display), 1 page, as downloaded Aug. 30, 2020.*

Ulla Ravn et al., "Deep sequencing of phage display libraries to support antibody discovery", Methods, Mar. 1, 2013, pp. 99-110, vol. 60, No. 1.
Peter A.C. 'T Hoen et al., "Phage display screening without repetitious selection rounds", Analytical Biochemistry, Feb. 1, 2012, pp. 622-631, vol. 421, No. 2.
Extended European Search Report in EP Application No. 14864675.5 dated May 11, 2017.
Smith, George P., "Filamentous Fusion Phage: Novel Expression Vectors That Display Cloned Antigens on the Virion Surface", Science, Jun. 14, 1985, pp. 1315-1317, vol. 228 (4705).
John McCafferty et al., "Phage antibodies: filamentous phage displaying antibody variable domains", Letters to Nature, Dec. 6, 1990, pp. 552-554, vol. 348 (6301).
James D. Marks et al., "By-passing Immunization Human Antibodies from V-gene Libraries Displayed on Phage", J. Mol. Biol. Dec. 5, 1991, pp. 581-597, vol. 222 (3), Academic Press Limited.
Yuji Ito et al., "Isolation and identification of the specific antibodies using comprehensive sequence analysis from antibody phage library", Program and Abstracts for the 13th Annual Meeting of the Protein Science Society of Japan, held on Jun. 12 to 14, 2013, published May 31, 2013, pp. 47 and 40.
Yuji Ito et al., "Isolation and identification of the specific antibodies using comprehensive sequence analysis from antibody phage library", Material for presentation on Jun. 14, 2013 in the 12th Annual Meeting of the Protein Science Society of Japan.
Yuji Ito, "Isolation and Characterization of Antigen-specific VHH Antibodies from Immunized Alpaca VHH Antibody Phage Library Using Next Generation Sequencing (NGS)", Website copy of a list of Poster Presentations for IBC's 24th Annual Antibody Engineering & Therapeutics, updated on Nov. 6, 2013.
International Search Report in PCT Application No. PCT/JP2014/080853, dated Feb. 10, 2015.
Written Opinion of the ISA in PCT Application No. PCT/JP2014/080853, dated Feb. 10, 2015.

* cited by examiner

*Primary Examiner* — G Steven Vanni
(74) *Attorney, Agent, or Firm* — Hauptman Ham, LLP

(57) ABSTRACT

A method determines an amino acid sequence that binds to a target molecule or a base sequence encoding the same. The method pans for bringing a library constructed by a display method, followed by incubation. The method sequences for analyzing a base sequence before panning step and the polypeptide group of the library after panning by a next-generation sequencer, or determining an amino acid sequence based on a base sequence obtained by analyzing the base sequence of a nucleic acid encoding all the polypeptides by a next-generation sequencer. The method scores for evaluating and scoring, based on the results of the sequencing step, an amplification ratio. The method determines a sequence for selecting a polypeptide with a high score and determines an amino acid sequence of the polypeptide or a base sequence as an amino acid sequence that binds to the target molecule or as a base sequence of a nucleic acid encoding the polypeptide.

12 Claims, 1 Drawing Sheet
Specification includes a Sequence Listing.

[Fig.1]
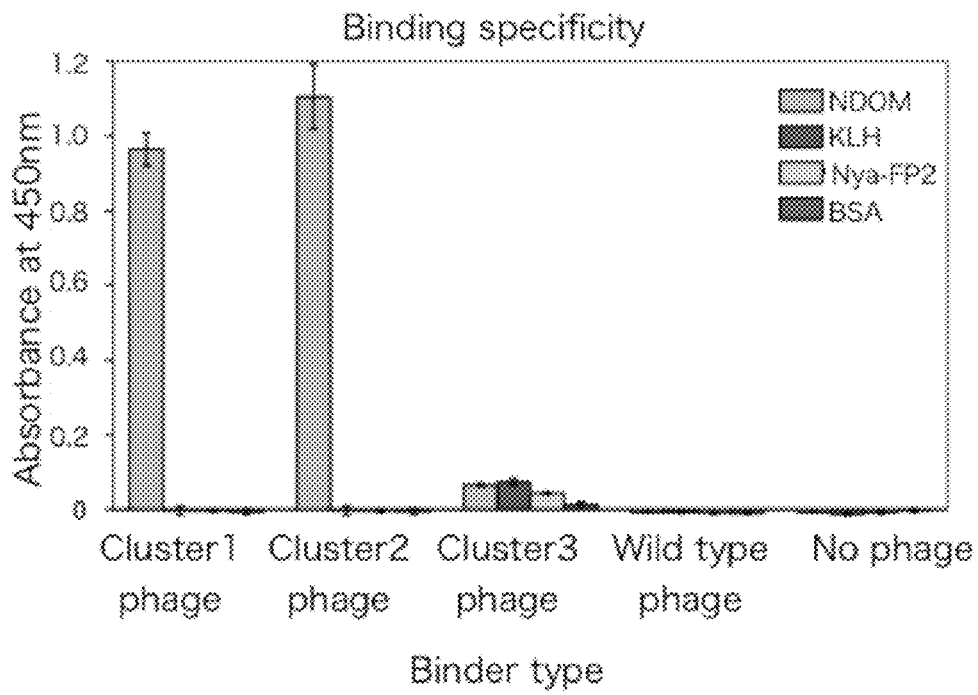
[Fig.2]
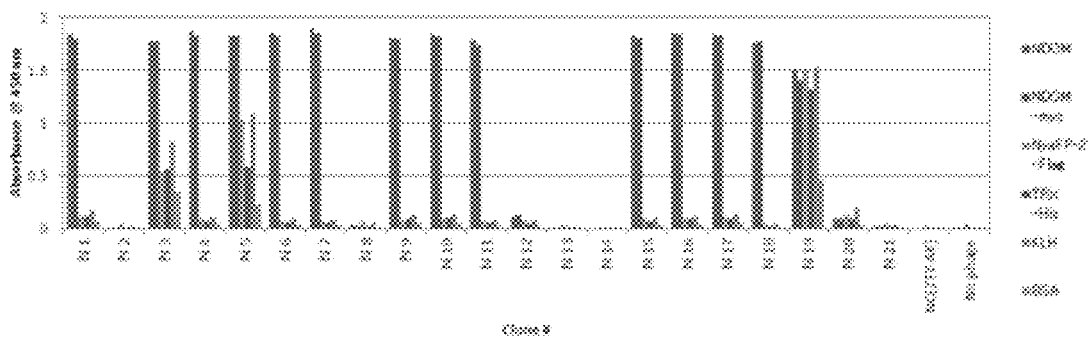
[Fig 3]
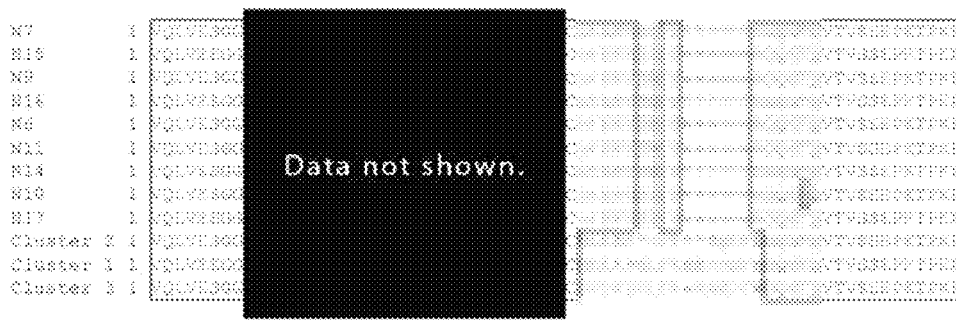

SEQUENCE LISTING

<160> NUMBER OF SEQ ID NOS: 2

<210> SEQ ID NO 1
<211> LENGTH: 8
<212> TYPE: PRT
<213> ORGANISM: Alpcaca

<400> SEQUENCE: 1

Val Gln Leu Val Glu Ser Gly Gly
1               5

<210> SEQ ID NO 2
<211> LENGTH: 12

```
<212> TYPE: PRT
<213> ORGANISM: Alpaca

<400> SEQUENCE: 2

Val Thr Val Ser Ser Glu Pro Lys Thr Pro Lys Pro
1               5                   10
```

METHOD FOR DETERMINING AND SYSTEM FOR DETERMINING POLYPEPTIDE BONDING TO TARGET MOLECULE

RELATED APPLICATIONS

The present application is a National Phase entry of International Application No. PCT/JP2014/080853, filed Nov. 21, 2014, which claims priority of Japanese Application No. 2013-242304, filed Nov. 22, 2013.

TECHNICAL FIELD

The present invention relates to a method of determining an amino acid sequence of a polypeptide that binds to a target molecule or a nucleic acid sequence encoding the polypeptide.

BACKGROUND ART

Recently, relationships between various diseases and biomolecules have been reported and molecular targeted drugs or molecular targeted therapies that target such disease-related molecules have been developed. Under such situations, a technology of designing an antibody, peptide, aptamer, or the like having high specificity and affinity to a predetermined target molecule and capable of interacting with the target molecule has been developed.

For example, a method of constructing a library including a variety of polypeptides and screening a polypeptide that binds to a target molecule from such a library has been used widely. For construction of a polypeptide library, a display method capable of associating a genotype with a phenotype has drawn attention and a phage display method, a ribosome display method, an mRNA display method, a cDNA display method, and the like have been developed.

Of these, the phage display method is most popular. In 1985, Smith G. P. reported the possibility of a protein being displayed on the surface of a filamentous phage (Non-Patent Document 1); in 1990, McCafferty J., et al. applied the method to preparation of a monoclonal antibody (Non-Patent Document 2); and in 1991, Smith G. P., et al. reported the possibility of scFv or Fab being also displayed on a phage (Non-Patent Document 3).

The phage display method includes a step called "panning" in which after construction, based on a gene sequence or the like of an antibody in the blood of an animal immunized with a target molecule as an antigen, of a phage library displaying the antibody or a fragment thereof, the phage on which the antibody or fragment that binds to the target molecule has been displayed is enriched. Panning is performed by preparing a solid-phase carrier having a target molecule immobilized thereon or a cell for expressing the target molecule therein, bringing that into contact with a phage library, and collecting the phage that has bound to the target molecule. Panning is typically repeated at least three to five times or so and the phage that binds to the target molecule is enriched gradually.

Then, *Escherichia coli* or the like is infected with a phage group obtained by panning, and a phage is rescued from about 40 to 100 *Escherichia coli* clones obtained on the plate. The phage thus obtained not only displays a polypeptide having binding ability to the target molecule but also stores therein genetic information of the antibody in the phage DNA so that this genetic information can also be used for the production of the antibody or fragment thereof.

As described above, the phage display method is highly useful as a method of isolating a polypeptide that binds to a target molecule. On the other hand, a step of infecting *Escherichia coli* clones with a phage and thereby selecting clones requires labor and time and only a limited number of *Escherichia coli* clones can be selected so that only phages greatly amplified by panning can be selected. For example, even when 100 clones are selected, it is difficult to obtain a molecule that is displayed on a phage that has a content of less than 1% in a library after panning. Polypeptides that bind to a target molecule available by this method are known to have a sequence very similar to each other, but it is desired to obtain, as a drug candidate, a plurality of polypeptides that binds to different sites of the target molecule.

PRIOR ART DOCUMENTS

Non-Patent Documents

Non-Patent Document 1: Smith G P, Science. 1985 Jun. 14; 228(4705): 1315-7.
Non-Patent Document 2: McCafferty J et al., Nature. 1990 Dec. 6; 348(6301): 552-4.
Non-Patent Document 3: Marks J D et al., J Mol Biol. 1991 Dec. 5; 222(3): 581-97.

SUMMARY

Problem to be Solved

An object of the present invention is to provide a method for finding a target-molecule-binding polypeptide from a library constructed by a display method capable of associating a polypeptide with a nucleic acid encoding it, wherein the polypeptide is one that cannot be found by a method of infecting a phage obtained by repeating conventional panning with *Escherichia coli* and cloning it; and to provide a method for designing, based on the amino acid sequence or nucleic acid sequence information of the polypeptide, a polypeptide that binds to the target molecule.

Solution to Problem

As a result of researches conducted with a view to overcoming the above-described problem, the present inventor has found that even polypeptides that can be amplified only slightly by panning can be selected by carrying out panning only once while using a polypeptide library constructed using a display method and comprehensively analyzing and comparing the sequence information of polypeptides included in the library before and after panning by a next generation sequencer. It has also been found that a polypeptide group thus selected is classified into clusters based on their sequence and based on the similarity of the sequence of polypeptides belonging to each of the clusters, the sequence of a polypeptide capable of binding to a target molecule can be determined. As a result, the inventor has succeeded in solving the problem of the present invention.

Described specifically, the present invention relates to:

[1] a method of determining an amino acid sequence of a polypeptide that binds to a target molecule or a base sequence of a nucleic acid encoding the polypeptide, including:

a panning step for bringing a library constructed by a display method capable of associating polypeptides with nucleic acids encoding the polypeptides into contact with the target molecule, followed by incubation to obtain a polypeptide group that binds to the target molecule;

a sequencing step for analyzing a base sequence of a nucleic acid encoding all the polypeptides belonging to the polypeptide group of the library before the panning step and the polypeptide group of the library after the panning step by a next-generation sequencer, or determining an amino acid sequence based on a base sequence obtained by analyzing the base sequence of a nucleic acid encoding all the polypeptides by a next-generation sequencer;

a scoring step for evaluating and scoring, based on the results of the sequencing step, an amplification ratio of each of the polypeptides by the panning; and a sequence determination step for selecting a polypeptide with a high score and determining an amino acid sequence of the polypeptide or a base sequence of a nucleic acid encoding the polypeptide as an amino acid sequence of a polypeptide that binds to the target molecule or as a base sequence of a nucleic acid encoding the polypeptide;

[2] the method as described above in [1],
wherein in the scoring step, based on the results of the sequencing step, at least one value selected from the group consisting of:

an amplification ratio of a proportion of a predetermined sequence xi between the library before the panning step and the library after the panning step;

an amplification ratio of, when sequences after the panning step are clustered, a cluster to which the predetermined sequence xi belongs between the library before the panning step and the library after the panning step;

a statistic change of, when sequences after the panning step are clustered, a cluster to which the predetermined sequence xi belongs between the library before the panning step and the library after the panning step;

an amplification ratio of, when sequences after the panning step are clustered, each of the sequences belonging to a cluster to which the predetermined sequence xi belongs between the library before the panning step and the library after the panning step; and a statistic of, when sequences after the panning step are clustered, amplification ratio groups of each of the sequences belonging to a cluster to which the predetermined sequence xi belongs between the library before the panning step and the library after the panning step;

is determined and based on the determined value, scoring is performed;

[3] the method as described above in [2], wherein the amplification ratio of a cluster to which the predetermined sequence xi belongs is evaluated by determining a central value in a population of contents, in the library, of each of the sequences belonging to the cluster, that is, at least one value selected from the group consisting of a mean, a median, and a mode;

[4] the method as described above in [2], wherein the statistic change of a cluster to which the predetermined sequence xi belongs is evaluated by determining a statistic in a population of a content, in the library, of each of the sequences belonging to the cluster, that is, at least one value selected from the group consisting of a variance, a standard deviation, a sample standard deviation, an unbiased variance, a mean, a median, and a mode;

[5] the method as described above in [2], wherein the statistic of an amplification ratio of each of the sequences belonging to a cluster to which the predetermined sequence xi belongs is evaluated by determining a statistic in a population of the amplification ratio of each of the sequences belonging to the cluster, that is, at least one value selected from the group consisting of a variance, a standard deviation, a sample standard deviation, an unbiased variance, a mean, a median, and a mode;

[6] the method as described above in [1], wherein in the scoring step, based on the results of the sequencing step, at least one of:

an amplification ratio of a proportion of a predetermined sequence xi between the library before the panning step and the library after the panning step;

an amplification ratio of, when sequences after the panning step are clustered, a cluster to which the predetermined sequence xi belongs between the library before the panning step and the library after the panning step;

a statistic change of, when sequences after the panning step are clustered, a cluster to which the predetermined sequence xi belongs between the library before the panning step and the library after the panning step;

an amplification ratio of, when sequences after the panning step are clustered, each of the sequences belonging to a cluster to which the predetermined sequence xi belongs between the library before the panning step and the library after the panning step; and a statistic of, when sequences after the panning step are clustered, amplification ratio groups of each of the sequences belonging to a cluster to which the predetermined sequence xi belongs between the library before the panning step and the library after the panning step;

is determined and based on the determined value, scoring is performed;

[7] the method as described above in any of [2] to [6], wherein the scoring step further includes:

a step of clustering, based on the results of the sequencing step, the polypeptide group included in the library after the panning step; and a step of, based on a score function represented by the following formula (I):

$$\text{Score}(x_i) = a \cdot \text{Amp}(x_i) \cdot b \cdot \text{Amp}C(x_i) \cdot c \cdot S(x_i) \quad \text{[Numerical formula 1]}$$

using Score(di) as a score when a nucleic acid sequence encoding a polypeptide that binds to the target molecule is determined, and using a score obtained from Score(di) and Score(pi) when an amino acid sequence of the polypeptide that binds to the target molecule is determined (wherein di represents a DNA sequence di, pi represents an amino acid sequence pi determined by converting the di, Amp(xi) represents an amplification ratio of a proportion of the sequence xi between before and after the panning step, AmpC(xi) represents an amplification ratio of a cluster to which xi belongs when each cluster is designated as Cn, S(xi) represents a variation of an amplification ratio of each of sequences belonging to C(xi) when the cluster to which xi belongs is designated as C(xi), and a, b, and c represent weight variables),

[8] the method as described above in [7], wherein in the sequence determination step, a polypeptide having a score of 80 or more as calculated in the scoring step is selected;

[9] the method as described above in any of [1] to [8], wherein the library includes, as a polypeptide, an antibody or an antigen-binding fragment thereof;

[10] the method as described above in any of [1] to [9], wherein the display method is a phage display method;

[11] the method as described above in [10], wherein the library is constructed based on a gene sequence of an antibody in the blood of an animal immunized with the target molecule;

[12] the method as described above in [10], wherein the library is constructed based on a gene sequence of an antibody in the blood of a non-immunized animal;

[13] the method as described above in [11] or [12], wherein the animal is an alpaca;

[14] a system for determining an amino acid sequence of a polypeptide that binds to a target molecule or a base sequence of a nucleic acid encoding the polypeptide according to the method as described above in any of [1] to [13], comprising:
an apparatus that evaluates and scores, based on the results of the sequencing step, an amplification ratio of each of the polypeptides through the panning;

[15] a system for determining an amino acid sequence of a polypeptide that binds to a target molecule or a base sequence of a nucleic acid encoding the polypeptide according to the method as described above in [6], comprising:
a first apparatus for calculating an amplification ratio of a proportion of the predetermined sequence xi between libraries before and after the panning step;
a second apparatus for calculating, when sequences after the panning step are clustered, an amplification ratio of a cluster to which the predetermined sequence xi belongs between libraries before and after the panning step;
a third apparatus for calculating, when sequences after the panning step are clustered, an amplification ratio of each of sequences belonging to a cluster to which the predetermined sequence xi belongs or a variance of the amplification ratio between before and after the panning step; and
a fourth apparatus for calculating a score of the sequence xi in accordance with the value calculated by at least one of the first to third apparatuses;

[16] a system for determining an amino acid sequence of a polypeptide that binds to a target molecule or a base sequence of a nucleic acid encoding the polypeptide according to the method as described above in [7], comprising:
an apparatus for calculating Amp(xi),
an apparatus for calculating AmpC(xi),
an apparatus for calculating S(xi), and
an apparatus for calculating Score(xi);

[17] the system as described above in any of [14] to [16] further comprising a next-generation sequencer; and

[18] the system as described above in any of [14] to [17], further comprising an apparatus for clustering, based on the results of the sequencing step, the polypeptide group included in the library after the panning step.

Advantageous Effects of Invention

According to the present invention, an amino acid sequence of a polypeptide that binds to a target molecule or a base sequence of a nucleic acid encoding the polypeptide can be determined by the steps of single panning, analysis using a next-generation sequencer, and calculation based on the analysis results.

A trace amount of a polypeptide contained in a sample cannot be found by a conventional method using a plurality of times of panning and cloning with *Escherichia coli*. According to the present invention, however, such a trace amount of a polypeptide it can be found as a polypeptide that binds to a target molecule and at the same time, a polypeptide having a variety of sequences can be obtained.

In addition, the sequence of an intended polypeptide can be determined rapidly because enormous labor necessary for a cloning step with *Escherichia coli* can be omitted.

The polypeptide thus obtained that specifically binds to a target molecule is useful for the development of drugs or reagents.

BRIEF DESCRIPTION OF DRAWINGS

FIG. 1 shows the ELISA analysis results of binding specificity, to an antigen, of an antibody obtained by the method according to the present invention;

FIG. 2 shows the ELISA analysis results of binding specificity, to an antigen, of an antibody obtained by the conventional method; and FIG. 3 shows comparison in sequence between an antibody obtained by the method according to the present invention and an antibody obtained by the conventional method.

DESCRIPTION OF EMBODIMENTS (Panning Step)

The "method of determining an amino acid sequence of a polypeptide that binds to a target molecule or a base sequence of a nucleic acid encoding the polypeptide" according to the present invention includes a panning step for bringing a library constructed by a display method capable of associating a polypeptide with a nucleic acid encoding it into contact with the target molecule, followed by incubation to obtain a group of polypeptides that bind to the target molecule.

The term "target molecule" as used herein is not particularly limited, and, for example, it may be an in vivo disease-related molecule involved in onset or progress of a disease. No particular limitation is imposed on the disease-related molecule insofar it is a molecule to which a polypeptide binds. Examples may include nucleic acids, polypeptides, saccharides, and lipids.

The term "polypeptide" as used herein means a molecule obtained by peptide bonding of two or more amino acids and it is used as a concept embracing peptides and proteins. The degree of the affinity of the "polypeptide that binds to a target molecule" herein is not particularly limited insofar as the polypeptide binds to a target molecule. In addition, the polypeptide may or may not have physiological active effects on the target molecule. The "polypeptide that binds to a target molecule" is sometimes called herein "target-molecule-binding polypeptide".

The number of amino acids of the target-molecule-binding polypeptide is not particularly limited herein and the polypeptide may be a small molecule usually called "peptide" or a protein having a function by itself such as an antibody, antigen-binding fragment thereof, or enzyme.

The "antibody" used herein has a structure which has two heavy chains (H chains) and two light chains (L chains) associated with each other and has been stabilized by a pair of disulfide bonds. The heavy chains are each composed of a heavy chain variable region VH, heavy chain constant regions CH1, CH2, and CH3, and a hinge region located between CH1 and CH2, while the light chains are each composed of a light chain variable region VL and a light chain constant region CL. Of these regions, a variable region fragment (Fv) composed of VH and VL is a region directly involved in antigen binding and provides the antibody with diversity. The antigen binding region composed of VL, CL, VH and CH1 is called "Fab region" and a region composed of the hinge region, CH2, and CH3 is called "Fc region".

The "antibody" used herein may be any isotype of IgG, IgM, IgA, IgD, and IgE. It may be obtained by immunizing a non-human animal such as mouse, rat, hamster, guinea pig, rabbit, chicken, or an animal of the family Camelidae (Bactrian camel, Arabian camel, llama, alpaca, and the like), it may be a recombinant antibody, or it may be a chimeric antibody, a humanized antibody, a fully humanized antibody, or the like. The "chimeric antibody" means an antibody obtained by linking fragments of antibodies derived from different species.

The term "humanized antibody" means an antibody substituted, by an amino acid sequence characteristic to a non-human-derived antibody, at a position of a human antibody corresponding thereto. Examples of it include antibodies which have heavy chains CDR1 to 3 and light chains CDR1 to 3 of the antibody prepared by immunizing a mouse and are derived from the human antibody in all the other regions including four framework regions (FR) of each of the heavy chains and light chains. Such an antibody may also be called "CDR grafted antibody". The term "humanized antibody" may sometimes include a human chimeric antibody.

The term "antigen binding fragment" of the antibody as used herein means a fragment of an antibody that maintains binding ability to an antigen. Examples of the antigen binding fragment include, but are not limited to, Fab composed of VL, VH, CL, and CH1 regions; F(ab')$_2$ having two Fabs connected to each other via a disulfide bond in a hinge region; Fv composed of VL and VH; a single-chain antibody scFv having VL and VH connected to each other via an artificial polypeptide linker; and a bispecific antibody such as diabody, scDb, tandem scFv, or leucine zipper type one.

Animals of the family Camelidae are known to have, in the blood thereof, an antibody composed only of VH (VHH antibody) and this VHH antibody is also embraced in the antigen binding fragment of the present invention.

In the present specification, the term "amino acid" is used in its broadest meaning and it embraces not only naturally occurring amino acids but also artificial amino acid variants and derivatives. Examples of the amino acid used herein include naturally occurring proteinogenic L-amino acids; D-amino acids; chemically modified amino acids such as amino acid variants and derivatives; naturally occurring non-proteinogenic amino acids such as norleucine, β-alanine, and ornithine; and chemically synthesized compounds having properties known in the art as characteristics of an amino acid. Examples of the non-naturally occurring amino acids include α-methylamino acids (such as α-methylalanine), D-amino acids, histidine-like amino acids (β-hydroxy-histidine, homohistidine, α-fluoromethyl-histidine, and α-methyl-histidine, and the like); amino acids (such as "homo" amino acids) having extra methylene in the side chain thereof, and amino acids (such as cysteic acid) obtained by substituting a carboxylic acid functional group amino acid in the side chain by a sulfonic acid group.

The amino acids used herein may be represented by a commonly used single-letter or three-letter code. The amino acid represented by single-letter code or three-letter code may include a variant or derivative thereof.

The "nucleic acid encoding the polypeptide" as used herein means a nucleic acid showing an amino acid sequence of the polypeptide in accordance with a genetic codon table. The term "nucleic acid" is used herein in its broadest meaning. It may be a natural nucleic acid such as DNA, RNA, LNA (Locked Nucleic Acid) or PNA (Peptide Nucleic Acid) or an artificial nucleic acid. It may be a chimeric nucleic acid containing two or more of them.

In the "method of determining an amino acid sequence of a polypeptide that binds to a target molecule or a base sequence of a nucleic acid encoding the polypeptide" according to the present invention, an amino acid sequence of the target molecule binding polypeptide may be determined or a base sequence of a nucleic acid encoding the target molecule binding polypeptide may be determined. The term "determining a sequence" used herein may be sometimes replaced by the term "designing a sequence".

The term 'library constructed by a display method capable of associating polypeptides with nucleic acids encoding the polypeptides' means a library which can associate each polypeptide (phenotype) with a corresponding nucleic acid (genotype) that encodes the polypeptide because each polypeptide contained in the library is associated with a corresponding nucleic acid that encodes the polypeptide. Examples of such a library include libraries constructed by a phage display method, an mRNA display method, a ribosome display method, a STABLE method or a CIS display method.

The term 'phage display method' as used herein means a method of inserting a nucleic acid that encodes a desired polypeptide into a phage DNA and thereby displaying the polypeptide on the surface of the phage in a form fused with a coat polypeptide (for example, g3p or g8p) of the phage (see Non-Patent Documents 1 to 3).

For example, when a library of phages displaying scFv is constructed, an immunization library is prepared as follows. First, after synthesis of cDNA from a total NRA prepared in a manner known in the art from the blood, cells, tissues, or the like of a non-human animal immunized with a target molecule, VH and VL genes are amplified by PCR while using a primer mixture specific to each sub type. Then, the genes are purified on an agarose gel and the purified genes are linked to each other using a linker DNA. To the scFv antibody gene thus formed, a necessary restriction enzyme recognition site is further added by PCR. After treatment with a restriction enzyme, the resulting product is connected to a phagemid vector to transform *Escherichia coli*.

By co-infecting the transformed *Escherichia coli* with a helper phage having a normal g3p gene or g8p gene, a phage library displaying scFv having a variety of sequences on the surface and having, packaged therein, a phagemid vector encoding the gene information of the scFv can be produced. Instead of infection with a helper phage, *Escherichia coli* expressing a g3p polypeptide or g8p polypeptide may be used as a host in an alternative method.

The "mRNA display method" described herein is a method also called "in vitro virus method" (Roberts R W and Szostak J W (1997) Proc. Natl. Acad. Sci. USA 94: 12297-12302; Nemoto N et al. (1997) FEBS Letters 414: 405-408).

Construction of a library by the mRNA display method is started first by artificially synthesizing a DNA or mRNA library, converting, if the DNA library is synthesized, it into an mRNA library with RNA polymerase, and then translating the mRNA library in a cell-free translation system. At this time, by constituting so that the mRNA and the expressed polypeptide bind to each other, the polypeptide (phenotype) binds to a nucleic acid (genotype) encoding the polypeptide to form one molecule. A method of binding the mRNA to the expressed polypeptide is not particularly limited, but a method of binding puromycin, which is a tRNA analog, to the 3' end of mRNA has been used widely.

The "ribosome display method" described herein is a method of producing a complex in which an mRNA and a polypeptide encoded thereby have been bound to each other via a ribosome. A library of such a complex is constructed by preparing an mRNA library and translating it in a cell-free translation system, as in the mRNA display method. During construction, the mRNA is designed so as not to include a stop codon and after a translation reaction, it is diluted with a solution containing an Mg ion at high concentration and then stored at 4° C. This enables stable storage of the complex.

The "STABLE method (Streptavidin-biotin linkage in emulsions)" described herein makes use of binding between streptavidin and biotin. First, a library of double-stranded DNAs to which biotin has been bound is constructed by PCR. As the double-stranded DNA, that encoding a fusion polypeptide of a polypeptide to be displayed and streptavidin is used. When the biotin-bound double-stranded DNA is transcribed and translated in an emulsion using a cell-free transcription translation system, the expressed streptavidin and biotin bind to each other to form a complex between the double-stranded DNA and the polypeptide.

The "CIS display method" is started by constructing a double-stranded DNA library including a start codon, a DNA encoding a polypeptide to be displayed, a DNA encoding a RepA polypeptide, a CIS sequence, and an on sequence in this order. Transcription and translation of the resulting library in a cell-free transcription translation system produce the polypeptide to be displayed and the RepA polypeptide. RNA polymerase then stops at the position of the CIS sequence. The RepA polypeptide binds to the ori sequence on the DNA, resulting in the formation of a complex of the polypeptide and the double-stranded DNA via interaction between the RepA polypeptide and the ori sequence.

In the method of determining an amino acid sequence of a polypeptide that binds to a target molecule or a base sequence of a nucleic acid encoding the polypeptide according to the present invention, a panning step is performed using a library constructed by any of these display methods.

The term "panning step" as used herein means a step of bringing a target molecule into contact with a library constructed by any of the display methods, incubating the resulting library to obtain a group of the polypeptide that binds to the target molecule. This step can be performed as needed by those skilled in the art, depending on the kind of the display methods.

For example, in the case of a library constructed using the phage display method, a target molecule is immobilized on the surface of a solid phase by a known method or a method based thereon and then a solution containing a phage library is added, followed by incubation. The solid phase surface is then washed with a buffer or the like to remove a phage that has remained unbound to the target molecule. A phage that has bound to the target molecule may then be eluted with an appropriate buffer or the like.

When the target molecule is a membrane polypeptide, cell panning may be performed by bringing cells into contact with the library. In this case, a method using a plate or membrane on which cells have been immobilized, a method of separating a phage that has bound to cells by repeating centrifugation, a method of isolating a phage bound to cells by a flow cytometer, or the like may be used.

The phage thus isolated stores therein a DNA encoding a polypeptide having binding ability to the target molecule.

Also when a library is constructed by the mRNA display method or ribosome display method, a target molecule is immobilized on the surface of a solid phase by a known method and a solution containing an mRNA-polypeptide complex library is added, followed by incubation. Then, the surface of the solid phase is washed with a buffer or the like to remove an mRNA-polypeptide complex that has remained unbound to the target molecule. Then, an mRNA-polypeptide complex that has bound to the target molecule is eluted with an appropriate buffer or the like. Cell panning may be performed instead.

The mRNA-polypeptide complex thus obtained has an mRNA encoding a polypeptide having binding ability to the target molecule. Prior to analysis of the sequence by a next-generation sequencer, a cDNA may be synthesized from the mRNA by a reverse transcriptase.

Also when a library is constructed by the STABLE method or the CIS display method, a target molecule is immobilized on the surface of a solid phase by a known method and a solution containing a double-stranded DNA-polypeptide complex library is added, followed by incubation. Then, the surface of the solid phase is washed with a buffer or the like to remove a double-stranded DNA-polypeptide complex that has remained unbound to the target molecule. Then, a double-stranded DNA-polypeptide complex bound to the target molecule is eluted with an appropriate buffer or the like. Cell panning may be performed instead.

The double-stranded DNA-polypeptide complex thus obtained has a double stranded DNA encoding a polypeptide having binding ability to the target molecule. Prior to analysis of the sequence by a next-generation sequencer, a step of dissociating it into a single-stranded DNA may be performed.

(Sequencing Step)

The "method of determining an amino acid sequence of a polypeptide that binds to a target molecule or a base sequence of a nucleic acid encoding the polypeptide" according to the present invention next comprises a step of analyzing the base sequence of a nucleic acid encoding all the polypeptides of a polypeptide group of the library before the panning step and a polypeptide group of the library after the panning step by a next-generation sequencer; or analyzing the base sequence of a nucleic acid encoding them by a next-generation sequencer and determining an amino acid sequence based on the base sequence thus obtained.

The term "next-generation sequencer" as used herein is a term used in a concept for comparing it with a sequencer using a conventional Sanger method. The next-generation sequencer is also called "parallel sequencer", "massively parallel sequencer", "high-throughput sequencer", or the like. It means an apparatus capable of simultaneously decoding tens of thousands or billions of base sequence information at a time at a markedly high speed. The next-generation sequencer operates on various principles. Specific examples include, but not limited to, Genome Analyser•HiSeq•MiSeq (Illumina), SOLiD•IonTorrent (Life Technologies), PacBio (Pacific BioScience), Heliscope (Helicos), The Polonator (Dover Systems), 454 GS (Roche), or products using the technology of Oxford Nanopore Technologies.

The next-generation sequencer is preferably capable of analyzing a long sequence with high precision. When the precision is insufficient, an error may be corrected using data from another model.

The sequence analysis of the library before panning and the library after panning by a next-generation sequencer may be performed by those skilled in the art based on a known method, depending on the kind of the next-generation sequencer. The amino acid sequence may be determined easily by those skilled in the art based on the nucleic acid sequence obtained by sequencing.

(Scoring Step)

In the "method of determining an amino acid sequence of a polypeptide that binds to a target molecule or a base sequence of a nucleic acid encoding the polypeptide" according to the present invention, the sequencing step is followed by a scoring step for evaluating and scoring, based on the results of the sequencing step, an amplification ratio of each polypeptide through panning.

The step of "evaluating and scoring an amplification ratio of a polypeptide" described herein is a step of comparing a polypeptide included in the library after panning or a nucleic acid encoding the polypeptide with a polypeptide included in the library before panning or a nucleic acid encoding the polypeptide and evaluating and scoring how much a predetermined sequence is enriched by panning. Any method may be used for scoring.

An amplification ratio Amp(xi) of a proportion of the sequence xi before and after panning may be evaluated and scored, for example, supposing that di represents a DNA sequence obtained as a result of sequencing, pi represents a sequence obtained by converting the di into an amino acid, RB(xi) is a proportion of the sequence xi in the library before panning, and RA(xi) represents a proportion of the sequence (xi) in the library after panning. The term "proportion of the sequence xi in the library" as used herein means a proportion of the number of the sequence xi to a total number of sequences detected from the library.

In this case, the amplification ratio for DNA is evaluated as:

$$Amp(d_i) = \frac{RB(d_i)}{RA(d_i)} \quad \text{[Numerical formula 2]}$$

and the amplification ratio for polypeptide is evaluated as $$Amp(p_i) = \frac{RB(p_i)}{RA(p_i)} \quad \text{[Numerical formula 3]}$$

and the ratio thus obtained can used as a score.

Alternatively, after clustering polypeptides included in the library after the panning step by a predetermined method, an amplification ratio AmpC(xi) of each cluster to which the sequence xi belongs may be evaluated and scored. The amplification ratio AmpC(xi) may be defined by the formula described below; or may be determined by finding, with respect to clusters before and after panning, all the values for describing the central value of the population and comparing them from each other. The term "all the values for describing the central value of the population" may be, for example, at least one value selected from the group consisting of a mean, a median, and a mode of the cluster or an amplification ratio of the cluster.

Polypeptides may be clustered by a known method based on the amino acid sequence thereof or the base sequence of a nucleic acid encoding them. Examples of it include, but not limited to, multiple sequence alignment program Clustal series (Clustal W, Clustal X, and Clustal ω) or T-coffee. Better results can be expected by the optimization of score matrix or clustering algorism during calculating homology between sequences.

In this case, an amplification ratio for DNA is evaluated as:

$$AmpC(d_i) = \frac{\sum_{i \subset C(di)} RB(i)}{\sum_{i \subset C(di)} RA(i)} \quad \text{[Numerical formula 4]}$$

and an amplification ratio for polypeptide is evaluated as:

$$AmpC(p_i) = \frac{\sum_{i \subset C(pi)} RB(i)}{\sum_{i \subset C(pi)} RA(i)} \quad \text{[Numerical formula 5]}$$

and the values thus obtained can be used as a score.

Polypeptides included in the library after panning are clustered by a predetermined method and supposing that C(xi) represents a cluster to which a sequence xi belongs, the statistic of each sequence belonging to C(xi), an amplification ratio, or the statistic thereof may be evaluated and scored. Here, the variance S(di) of an amplification ratio is evaluated and scored. The statistic, amplification ratio, or statistic thereof may be defined by the below-described formula S(di); or it may be determined by finding, with respect to each sequence belonging to a cluster to which the sequence xi before and after panning belongs, all the values for describing the central value of the population and comparing them from each other. All the values for describing the central value of the population may be, for example, at least one value selected from the group consisting of a variance, a standard deviation, a sample standard deviation, an unbiased variance, a mean, a median, and a mode of each sequence belonging to the cluster or an amplification ratio of each sequence.

In this case, the amplification ratio for DNA is evaluated as:

$$S(di) = \sqrt{\sum_{i \in C(di)} \overline{(Amp(i) - Amp(i))}} \quad \text{[Numerical formula 6]}$$

and the amplification ratio for polypeptide is evaluated as:

$$S(pi) = \sqrt{\sum_{i \in C(pi)} \overline{(Amp(i) - Amp(i))}} \quad \text{[Numerical formula 7]}$$

and the values thus obtained may be used as a score.

Evaluation of an amplification ratio may be performed by using in combination two or more of: the amplification ratio Amp(xi) of a proportion of the sequence xi; the amplification ratio AmpC(xi) of a cluster to which xi belongs; and the amplification ratio S(xi) of each sequence belonging to the cluster C(xi) to which xi belongs; each described above. When these components are used in combination, they may each be weighted arbitrarily.

For example, Score (xi) can be defined as follows using all of the three components.

$$\text{Score}(x_i) = a \cdot \text{Amp}(x_i) \cdot b \cdot \text{Amp}C(x_i) \cdot c \cdot S(x_i) \quad \text{[Numerical formula 8]}$$

In the above formula, a, b, and c are each a weight variable. In order to equally weight the three components, they may all be set at 1.

(Sequence Determination Step)

In the "method of determining an amino acid sequence of a polypeptide that binds to a target molecule or a base sequence of a nucleic acid encoding the polypeptide" according to the present invention, the above-described step is followed by a step of selecting a polypeptide with a high score, specifying an amino acid sequence of it or a base sequence of a nucleic acid encoding it, and determining the resulting amino acid sequence or base sequence as an amino acid sequence of a polypeptide that binds to a target substance or a base sequence of a nucleic acid encoding the polypeptide.

This present step may be performed as needed by those skilled in the art based on the score determined for each sequence in the scoring step. As will be described later in Examples, when a sequence with a score of 80 or more was selected with the above-described Score(xi) as a score function, a polypeptide having the sequence specifically bound to a target molecule.

(System)

Each step of the "method of determining an amino acid sequence of a polypeptide that binds to a target molecule or a base sequence of a nucleic acid encoding the polypeptide" according to the present invention can be implemented by a hardware for specific purpose or a hardware for general purpose.

One example of the "system for determining an amino acid sequence of a polypeptide that binds to a target molecule or a base sequence of a nucleic acid encoding the polypeptide" according to the present invention is a system comprising:

a first analyzer for implementing a step of calculating an amplification ratio of a proportion of the predetermined sequence xi between the library before the panning step and the library after the panning step;

a second analyzer for implementing a step of calculating, when sequences after the panning step are clustered, an amplification ratio of a cluster to which the predetermined sequence xi belongs between the library before the panning step and the library after the panning step;

a third analyzer for implementing a step of calculating, when sequences after the panning step are clustered, an amplification ratio of each sequence belonging to a cluster to which the predetermined sequence xi belongs or a variance thereof between the library before the panning step and the library after the panning step; and a fourth analyzer for implementing a step of calculating, when an amplification ratio file made by at least one of the first to third analyzers is input, a score of the predetermined sequence in accordance with a predetermined score function.

The first analyzer may be an apparatus for implementing a step of calculating the above-described Amp(xi), the second analyzer may be an apparatus for implementing a step of calculating the above-described AmpC(xi), the third analyzer may be an apparatus for implementing a step of calculating the above-described S(xi), and the fourth analyzer may be an apparatus for implementing a step of calculating the above-described Score(xi).

The system according to the present invention may include a next-generation sequencer. A sequence file relating to a sequence decoded by the next-generation sequencer is input into the first to third analyzers and an amplification ratio is calculated in each analyzer.

The system according to the present invention may further include a fifth analyzer for implementing a step of clustering, based on the results of the sequencing step, sequences included in the library after the panning step. In this case, a sequence file relating to sequences decoded by the next-generation sequencer is input into the fifth analyzer, the sequences are clustered by a known method, and the file relating to clustering is delivered to the second analyzer or third analyzer.

Disclosure of all the patent documents and non-patent documents cited herein is incorporated herein by reference in its entirety.

Examples

The present invention will hereinafter be described specifically by Examples, but the present invention is not limited to or by them. The present invention can be modified into various modes without departing from the spirit of the present invention and such modifications are also embraced within the scope of the present invention.

1. Construction of Display Library

In the present research, an alpaca VHH antibody phage display library was used. Alpaca was immunized on Day 0, Day 14, and Day 28 with NDOM (N-domain of izumol protein) bound to KLH. Peripheral blood mononuclear cells were collected from 400 ml of the blood collected on Day 48 and mRNA in a VHH region was converted into cDNA by a reverse transcriptase.

A phage display library was obtained by ligating the PCR-amplified cDNA with a M13 phagemid vector, infecting it, together with a helper phage, into *E. coli*, and amplifying them. The resulting phage display library will hereinafter be called "pre-panning library".

2-1. Panning Step

Biopanning was performed by adding the pre-panning library to a solid-phased NDOM. After washing five times with PBST, a phage group displaying a VHH antibody that binds to the NDOM was eluted with 0.1 M glycine-HCL (pH 2.2). The resulting phage group will hereinafter be called "post-panning library".

2-2. Large-Scale Sequencing

The pre-panning library and the post-panning library obtained by the above-described procedure were sequenced using MiSeq of Illumina, Inc. They were sequenced both from the upstream and the downstream of the VHH region, followed by assembling to obtain a VHH sequence group. As a result, 65098 sequences (43823 kinds) translated into a polypeptide were obtained from the pre-panning library and 80662 antibody sequences (47518 kinds) were obtained from the post-panning library.

2-3. Comparative Analysis of Pre-Panning and Post-Panning Libraries 2-3-1. Sequence Amplification Ratio The proportion of each DNA sequence included in the pre-panning library and the proportion of each DNA sequence included in the post-panning library were compared and an amplification ratio of each DNA sequence was calculated. A similar operation was performed also for amino acid sequence. In the below-described formulae: di represents each DNA sequence; pi represents sequence obtained by converting di into an amino acid sequence; xi represents a symbol replaceable by either di or pi; RB(xi) represents a proportion of the sequence xi in the pre-panning library; and RA(xi) represents a proportion of the sequence xi in the post-panning library; and Amp(xi) represents an amplification ratio of a proportion of the sequence xi between the panning before and after.

$$Amp(d_i) = \frac{RB(d_i)}{RA(d_i)} \qquad \text{[Numerical formula 9]}$$

$$Amp(p_i) = \frac{RB(p_i)}{RA(p_i)} \qquad \text{[Numerical formula 10]}$$

2-3-2. Cluster Amplification Ratio

Sequence clustering was performed. Each cluster is designated as Cn. An amplification ratio AmpC(xi) of a cluster to which xi belongs is defined as follows.

$$AmpC(d_i) = \frac{\sum_{i \subset C(di)} RB(i)}{\sum_{i \subset C(di)} RA(i)} \qquad \text{[Numerical formula 11]}$$

$$AmpC(p_i) = \frac{\sum_{i \subset C(pi)} RB(i)}{\sum_{i \subset C(pi)} RA(i)} \qquad \text{[Numerical formula 12]}$$

2-3-3. Variance of Amplification Ratio in Cluster

A cluster to which xi belongs is designated as C(xi). An amplification ratio of each sequence belonging to C(xi) was calculated and its variance was determined.

$$S(di) = \sqrt{\sum_{i \in C(di)} \overline{(Amp(i) - Amp(i))}} \qquad \text{[Numerical formula 13]}$$

$$S(pi) = \sqrt{\sum_{i \in C(pi)} \overline{(Amp(i) - Amp(i))}} \qquad \text{[Numerical formula 14]}$$

2-3-4. Scoring

A score function Score(xi) was defined as follows. In the following formula, a, b, and c are each a weight variable. In the present example, calculation was made supposing that they were all 1.

$$Score(x_i) = a \cdot Amp(x_i) \cdot b \cdot AmpC(x_i) \cdot c \cdot S(x_i) \qquad \text{[Numerical formula 15]}$$

When a molecule to be designed is a base sequence such as a nucleic acid aptamer, a value obtained by calculation (such as arithmetic mean or geometric mean) making use of only Score(di) is used, while when a molecule to be designed is a polypeptide, a value obtained by calculation (such as arithmetic mean or geometric mean) making use of Score(di) and Score(pi) is used. In the present example, an antibody was the molecule to be designed so that the latter score was used. Scores of all the sequences were normalized such that the maximum score corresponded to 100 and the minimum score corresponded to 0 and thus, a final score was determined.

By using phages (Cluster 1 phage and Cluster 2 phage) displaying a polypeptide having a final score of 80 or higher and a phage (Cluster 3 phage) displaying a polypeptide having a score of 62, binding to each of NDOM, KLH, Nya-FP2, and BSA was analyzed by ELISA. The results are shown in FIG. 1. Cluster 1 phage and Cluster 2 phage bound to NDOM with high selectivity. Cluster 3 phage showed non-specific binding and had low affinity to any of the targets.

3. Antibody Obtained by Conventional Method

A phage binding to NDOM was isolated by a conventional method (cloning with *Escherichia coli*) and specificity of a VHH antibody displayed on the phage was verified by ELISA. The results are shown in FIG. 2. Eleven clones showed specificity to NDOM.

4. Comparison Between Method of Present Invention and Conventional Method

Antibody sequences obtained by the conventional method and those obtained by the method of the present invention were compared. The results are shown in FIG. 3.

Sequences obtained by the conventional method have a name beginning with N. Sequences obtained newly by the method of the present invention are expressed by Cluster 1 and Cluster 2. Sequences visible in FIG. 3 match either SEQ ID: 1 or SEQ ID: 2 of the sequence listing included as part of the application. It has been found that antibodies obtained by the conventional method are similar in sequence, but antibodies obtained by the method according to the present invention are largely different in sequence from each other. In addition, one of the antibodies obtained by the method according to the present invention has an amino acid sequence that is the same as that of N10.

The above findings have revealed that the method of the present invention can provide antibodies having both a novel sequence as well as a sequence available by the conventional method.

---

What is claimed is:

1. A method of determining an amino acid sequence of a polypeptide that binds to a target molecule or a base sequence of a nucleic acid encoding the polypeptide, said method comprising:
- a panning process comprising bringing a library of polypeptide molecules into contact with the target molecule followed by incubation to obtain a polypeptide group that binds to the target molecule;
- a sequencing process (a) or (b):
  - (a) before and after the panning process, performing a sequencing process comprising determining, using a next-generation sequencer, base sequences of one or more nucleic acids encoding all the polypeptides belonging to the polypeptide group or
  - (b) before and after the panning process, performing a sequencing process comprising determining one or more amino acid sequences corresponding to base sequences of one or more nucleic acids encoding all the polypeptides belonging to the polypeptide group, the base sequences obtained using a next-generation sequencer
- a scoring process comprising computing, based on the sequences before and after the panning process obtained in the sequencing process, an amplification ratio of each of the polypeptides in the polypeptide group resulting from the panning process, to determine a score for the polypeptides in the polypeptide group; and
- a sequence determination process comprising selecting a polypeptide from the polypeptide group that has a score, as determined in the scoring process, that is higher than the score of at least one other polypeptide in the polypeptide group and determining an amino acid sequence of the selected polypeptide or a base sequence of a nucleic acid encoding the selected polypeptide.

2. The method according to claim 1, wherein the scoring process determines at least one value selected from the group consisting of:
- an amplification ratio of a proportion of a predetermined sequence before the panning process to a proportion of the predetermined sequence after the panning process;
- in relation to clusters of sequences identified after the panning process, an amplification ratio of a proportion, before the panning process, of a cluster to which the predetermined sequence belongs to a proportion, after the panning process, of the cluster;
- in relation to clusters of sequences identified after the panning process, a change in a statistical parameter of a cluster to which the predetermined sequence belongs from before the panning process to after the panning process;
- in relation to clusters of sequences identified after the panning process, an amplification ratio of a proportion, before the panning process, of each of the sequences belonging to a cluster to which the predetermined sequence belongs to a proportion, after the panning process, of each of the sequences belonging to the cluster; and
- in relation to clusters of sequences identified after the panning process, a statistic of amplification ratios of sequences belonging to a cluster to which the predetermined sequence belongs from before the panning process to after the panning process.

3. The method according to claim 2, wherein the statistic change of a cluster to which the predetermined sequence belongs is evaluated by determining a statistic of a population of the sequences of the cluster in the library selected from the group consisting of a variance, a standard deviation, a sample standard deviation, an unbiased variance, a mean, a median, and a mode.

4. The method according to claim 2, wherein the statistic of amplification ratios of sequences belonging to a cluster to which the predetermined sequence belongs is selected from the group consisting of a variance, a standard deviation, a sample standard deviation, an unbiased variance, a mean, a median, and a mode.

5. The method according to claim 2, wherein the scoring process further comprises:
- clustering, based on the one or more sequences obtained in the sequencing process, the polypeptides of the polypeptide group after the panning process and
- computing a score using the following formula:

$$\text{Score}(x_i) = a \cdot \text{Amp}(x_i) \cdot b \cdot \text{Amp}C(x_i) \cdot c \cdot S(x_i)$$

wherein, when a score is determined for a nucleic acid sequence encoding a polypeptide that binds to the target molecule, then $x_i$ is a DNA sequence and
when a score is determined for an amino acid sequence of a polypeptide that binds to the target molecule is determined, then $x_i$ is an amino acid sequence corresponding to a DNA sequence and
wherein $\text{Amp}(x_i)$ represents an amplification ratio of a proportion of the sequence $x_i$ from before the panning process to after the panning process,
$\text{Amp}C(x_i)$ represents an amplification ratio of a cluster $C(x_i)$ to which $x_i$ belongs from before the panning process to after the panning process,
$S(x_i)$ represents a variation of amplification ratios of sequences belonging to $C(x_i)$, and
a, b, and c represent weight variables.

6. The method according to claim 5, wherein in the sequence determination process, a polypeptide having a score of 80 or more as calculated in the scoring process is selected.

7. The method according to claim 1, wherein the library includes, as a polypeptide, an antibody or an antigen-binding fragment thereof.

8. The method according to claim 1, wherein the library is constructed using a phage display method.

9. The method according to claim 8, wherein the library is constructed based on a gene sequence of an antibody in the blood of an animal immunized with the target molecule.

10. The method according to claim 8, wherein the library is constructed based on a gene sequence of an antibody in the blood of a non-immunized animal.

11. The method according to claim 9, wherein the animal is an alpaca.

12. The method according to claim 10, wherein the animal is an alpaca.

* * * * *